Figure 1:
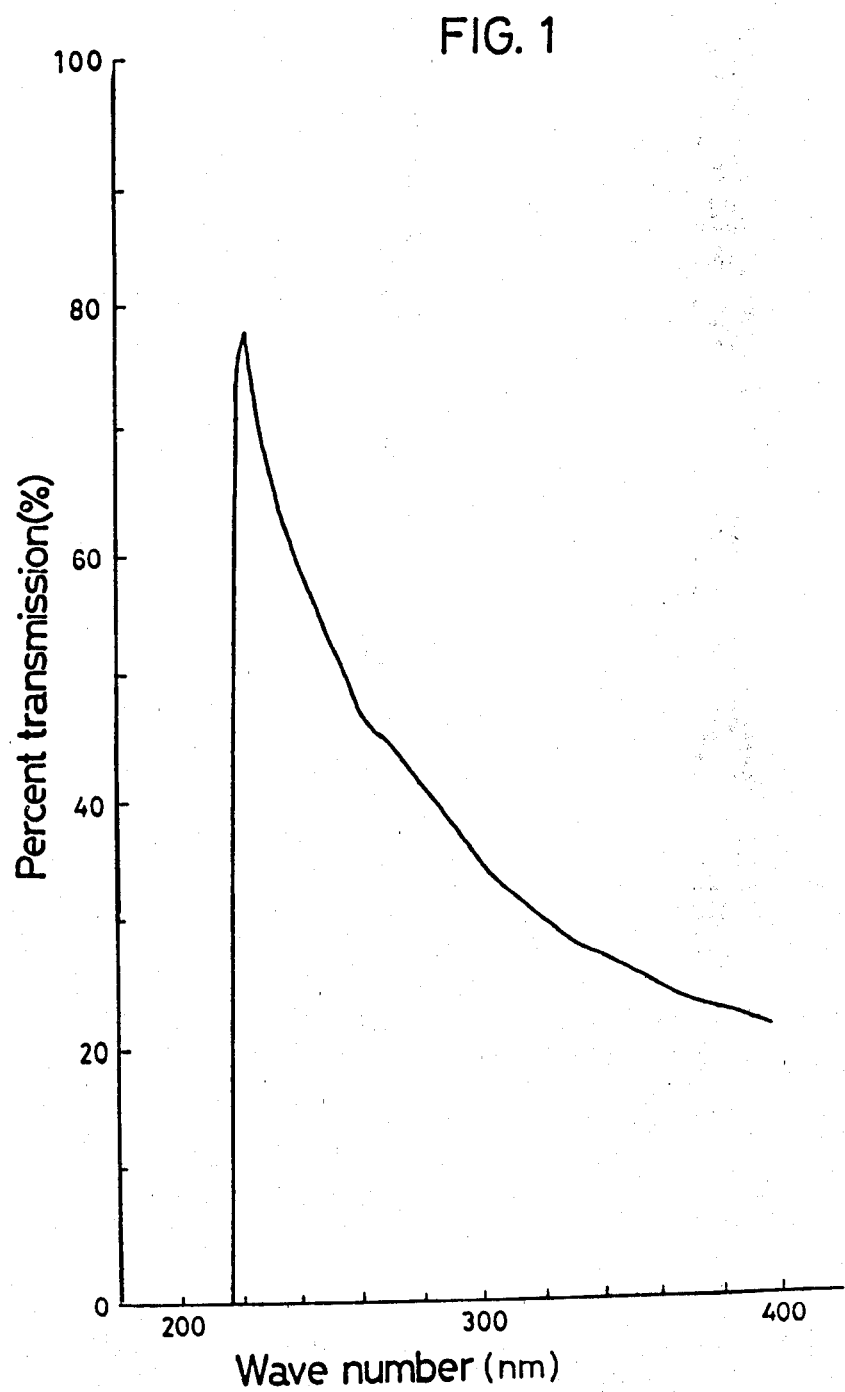

United States Patent [19]

Kojima et al.

[11] 4,419,349
[45] Dec. 6, 1983

[54] INTERFERON INDUCER, A PROCESS FOR PRODUCING THE SAME AND PHARMACEUTICAL COMPOSITION CONTAINING THE SAME

[75] Inventors: Yasuhiko Kojima, Yokohama; Seishi Konno, Tokyo; Sadao Tamamura, Tokyo; Yoshimoto Sano, Tokyo; Nobuyuki Shibukawa, Tokyo; Takashi Hashimoto, Chofu, all of Japan

[73] Assignee: The Kitasato Institute, Tokyo, Japan

[21] Appl. No.: 266,038

[22] Filed: May 22, 1981

Related U.S. Application Data

[63] Continuation-in-part of Ser. No. 97,609, Nov. 27, 1979, abandoned.

[30] Foreign Application Priority Data

Nov. 28, 1978 [JP] Japan ............................... 53-146976
Sep. 6, 1979 [JP] Japan ............................... 54-114623

[51] Int. Cl.$^3$ ............................................. A61K 35/78
[52] U.S. Cl. ..................................................... 424/195
[58] Field of Search ......................................... 424/195

[56] References Cited

FOREIGN PATENT DOCUMENTS

2036751 7/1980 United Kingdom ................ 424/195

*Primary Examiner*—Stanley J. Friedman
*Attorney, Agent, or Firm*—Wolder, Gross & Yavner

[57] ABSTRACT

An interferon inducer isolated from the plant tissue, having an elemental analysis of H: 8.5–8.7 %, C: 48.8–49 %, N: 6.3–6.5 % and P: 1.0–1.1 % and a molecular weight of from about 100,000 to about 3,000,000 (mainly about 200,000 to about 1,000,000) and containing as main constituents amino acids, sugars and phosphoric acid. This substance is believed to be a homogeneous polymer of protein and sugars, containing phosphoric acid. This substance has an excellent interferon inducing activity and low toxicity and is significantly active against various viruses. The interferon inducer may be produced by extracting a substance having interferon inducing activity from the tissue of a plant of the genus Perilla of the family Labiatae or a variant thereof containing said active substance and recovering the active substance from the extract thereby obtained. Preferably, the extraction may be effected with water and the recovery may be effected by ultrafiltration. Pharmaceutical composition of this invention comprises as active ingredient the interferon inducer of this invention in association with a pharmaceutical carrier or excipient.

13 Claims, 2 Drawing Figures

4,419,349

INTERFERON INDUCER, A PROCESS FOR PRODUCING THE SAME AND PHARMACEUTICAL COMPOSITION CONTAINING THE SAME

RELATED APPLICATION

This application is a continuation-in-part of Ser. No. 97,609 filed Nov. 27, 1979, now abandoned.

BACKGROUND OF THE INVENTION

This invention relates to interferon inducer, a process for producing the same, the use of the same and a pharmaceutical composition containing the same.

Interferon, hereinafter also referred to as IF is a substance capable of acting upon animal or human cells to inhibit the growth of a virus and is a type of protein liberated from the cell in response to viral infection. The activity of IF is specific with respect to an animal species and non-specific with respect to a viral species and may vary, with differing conditions used for its induction. It is also known that the growth of certain animal tumour type viruses may significantly be inhibited by IF under certain conditions.

A substance capable of acting upon animal or humans cells to induce IF is designated as an IF inducer. Thus an IF inducer is of potential interest in the prevention and treatment of various human and animal diseases caused by viral infection. However, various known IF inducers have never been used in practice for such a purpose because of certain serious defects. Thus, for example, U.S. Pat. No. 3,583,893 (1971) discloses the production of a double-stranded ribonucleic acid as an IF inducer originating from a microorganism and describes in its prior art statement that many substances including bacteria, viruses, polysaccharides, mitogenic agents, endotoxin and the like stumulate interferon formation but none is of interest for routine use because of their inter alia toxicity, antigenicity and infectiousness. It has thus been believed that IF inducers isolated from microorganisms are in general disadvantageous for therapeutic use because of their high toxicity.

Examples of known mitogenic agent isolated from the tissues of higher plants include phytohemagglutinin (PHA) [Wheelock, Science, 149:301 (1965) and J. Biol. Chem., 212: 607–615 (1955)], pokeweed mitogen [Friedman et al, Proc. Soc. Exp. Med., 125:90 (1967) and J. Exp. Med., 124:859–872 (1966)] and concanavallin A [Willen et al, Cell. Immunol., 6:110 (1973) and Methods of Carbohydrate Chemistry, Vol. VI. 108–110 (1972)] respectively isolated from the tissues of kidney bean, pokeweed and horse bean by extracting with a saline solution or buffer solution, treating the extracted solution with an alcohol, followed by purification with column chromatography. Due to their extremely low IF-inducing activity, however, no successful attempt has been made to use these mitogenic agents for preventing and treating various diseases caused by viral infection.

Other IF inducers isolated from higher plants are also known. That is, Kojima et al [Japanese Patent Application as laid open to public inspection as Kokai Koho 32107/78] disclosed an IF inducer which is believed to be a kind of heteropolymeric saccharide containing as main constituents hexose (48%), protein (5%) and uronic acid (40%) and having a molecular weight of more than 100,000. This substance is isolated from the root of *Angelica acutiloba* Kitagawa (known in Japan as Toki) by extracting the root with hot water to give an extracted solution, subjecting the same to dialysis to give a residue, adding acetone to the residue to give a precipitate and freeze-drying the same. The extracted solution may, if desired, be made up to a suitable quantity by concentrating under reduced pressure or by using a Diaflo membrane (MW 10,000), followed by dialysis. Subsequently, Kojima and Tamamura [Japanese Patent Application laid open to public inspection as Kokai Koho 99313/78] disclosed an IF inducer having a molecular weight of more than 20,000 (mainly more than 60,000) and containing as main constituents a 1-3 bonded glucose (hexose: more than 90%). This IF inducer is produced by extracting the peeling of a mulberry e.g. *Morus alba* L. or *M. bombycis* Koidzumi with hot water, adding an organic solvent to the extracted solution to give a precipitate, adding a small amount of water to the same, subjecting the mixture to dialysis to give a residue and freeze-drying the same. If desired, the solution after extraction or before dialysis may be made up to a suitable quantity either by concentrating under reduced pressure or by using a Diaflo membrane.

These two IF inducers isolated from the tissues of higher plants have high IF-inducing activity and low toxicity and may be obtained readily and cheaply. However, the cheap and abundant supply of the raw material may cease as a result of the continued use of these plants over many years as the source of Sino-Japanese traditional drugs.

SUMMARY OF THE INVENTION

The present invention is based upon the discovery that a substance which we have isolated from the tissue of various plants of the genus Perilla of the family Labiatae (known in Japan as the genus Shiso of the family Shiso) and variants thereof shows high IF-inducing activity and extremely low toxicity. Moreover, the isolation of the active substance may be effected readily and simply.

According to this invention, there is provided a substance having IF-inducing activity which is stable in the substantially pure form of an amorphous whitish powder and which possesses the following physico-chemical characteristics:

(1) Elemental analysis: H:8.5–8.7%; C:48.8–49%, N:6.3–6.5%, P:1.0–1.1%

(2) Molecular weight: About 100,000 to about 3,000,000 (mainly about 200,000–about 1,000,000).

(3) Melting or decomposing point: Melting point indefinite. Carbonized at about 220° C.

(4) Ultraviolet absorption spectrum: As shown in FIG. 1 (in 0.1 N NaOH solution) which is unchanged in water or 1 N NaOH solution.

Figure 2:
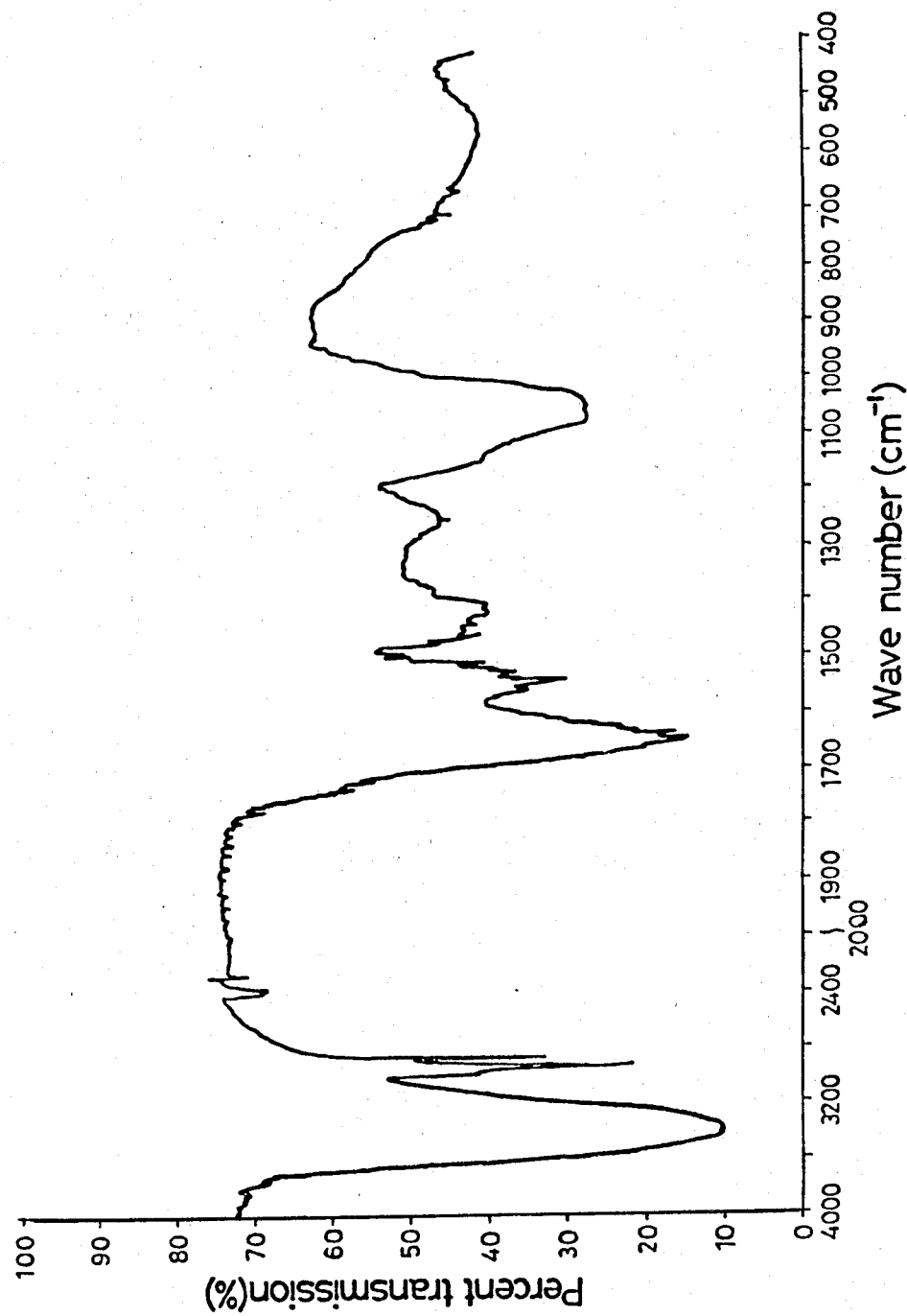

(5) Infrared absorption spectrum: As shown in FIG. 2 (by KBr method)

(6) Solubility in various solvents: Soluble in water, readily soluble in aqueous solution of sodium hydroxide, potassium hydroxide and ammonium hydroxide, and substantially insoluble in methanol, ethanol, propanol, butanol, acetone, chloroform and diethyl ether.

(7) Color reaction: Positive in ninhydrin reaction, phenol/sulfuric acid reation and Dittmer reaction. Negative in Folin's reagent and Elson-Morgan reaction.

(8) Nature: Acidic.

(9) Main chemical constituents:

(a) Amino acids (±0.3%): Oxyproline (3.2%), aspartic acid (9.3%), threonine (6.1%), serine (4.3%), glutamic acid (7.6%), proline (4.0%), glycine (10.0%), alanine (10.3%), valine (6.6%), isoleucine (5.4%), leucine (8.6%), phenylalanine (2.0%), lysine (3.9%), arginine (3.4%), tyrosine (trace), histidine (1.3%), ammonia (13.4%)

(b) Sugars (±0.3%): Arabinose (47.09%), galactose (25.66%), glucose (20.62%), mannose (4.64%), xylose (1.99%)

(10) Optical rotation: $[\alpha]_D^{25} = -75°$ to $-82°$ ($-79°$ in average) (c=0.47% in 0.1 N NaOH).

The elemental analysis of the active substance of this invention was determined by using a Perkin-Elmer Model 240 Elemental Analyzer (commercial product of Perkin-Elmer Corpn., U.S.A.). The molecular weight of the active substance of this invention was determined by analytical ultracentrifugation using a Spinco Model E Analytical Centrifuge (commercial product of Beckmann Instrument Inc., U.S.A.), ultrafiltration using an Amicon Ultrafilter with XM50, XM100A and XM300 membranes (commercial products of Amicon Corpn., U.S.A.) and UK10, UK50 and UK200 membranes (commercial products of Toyo Roshi K.K., Tokyo) and gel filtration using Sephadex G-200 (commercial product of Pharmacia Fine Chemicals AB., Sweden). The ultracentrifugation was effected under the following conditions and one broad peak having gentle slopes on both sides was observed: A sample (0.5-1.0%) of the active substance was suspended in a neutral solution of 0.1 M sodium chloride and centrifuged at 20° C. at a maximum run of 30,000 or 60,000 r.p.m. Supplementarily, column chromatography using gel filtration agents such as e.g. the series of Sepharose, Sephacryl (commercial products of Pharmacia Fine Chemicals AB., Sweden) and Bio-Gel (commercial products of Bio-Rad Laboratories Ltd., U.S.A.) was also used. All the results obtained were compared with the control values obtained, for example, by using standard references having identified molecular weights such as e.g. blue dextran 2000 (*$2 \times 10^6$), $\alpha_2$-macroglobulin from horse serum (*$8 \times 10^5$), thyroglobulin from bovine thyroid (*$6.69 \times 10^5$), catalase from bovine lever (*$2.1 \times 10^5$), aldolase from rabbit muscle (*$1.58 \times 10^5$) and albumin from bovine serum (*$6.7 \times 10^4$) [*.. standard molecular weight] Throughout various fractions having different molecular weights, substantailly the same elemental analysis and IF-inducing activity (determined by the method of hereinafter described Experiment 1) were found. From these results, in combination with a broad single band observed by the electrophoresis (cf. hereinafter described Experiment 2) and a high recovery ratio (cf. hereinafter described Experiment 4), it is found that the active substance of this invention is not a mixture but a high molecular weight polymer composed of polymers having substantially the same chemical and biological characteristics, of which major portion is present in a range of from about 200,000 to about 1,000,000 and the minor portion is present in a range of from about 100,000–about 200,000 and about 1.000.000–about 3,000,000.

The UV and IR absorption spectra were determined respectively by using Hitachi 340 Recording Spectrophotometer (commercial product of Hitachi Limited,. Japan) and Shimazu Recording Infrared Spectrophotometer IR-27G (commercial product of Shimazu Seisaku-sho, Japan).

The amino acids present were determined by hydrolysis with 6 N HCl at 110° C. for 48 hours in vacuo, followed by analysis using a Technicon Amino Acid Autoanalyzer Type NC-1 (commercial product of Technicon Corpn., U.S.A.) and the sugars present were determined by hydrolysis with 0.1 N sulfuric acid at 80° C. for 20 minutes and with 1 N sulfuric acid at 100° C. for 2 hours respectively, followed by analysis using a Technicon Sugar Autoanalyzer Type N-1 (commercial product of Technicon Corpn., U.S.A.).

The active substance of this invention also preferably and readily soluble in alkaline solutions and substantially insoluble in organic solvents.

The following tests were effected to ascertain that the active substance of this invention represents an IF inducer.

(1) IF-inducing activity:

Samples of the active substance of this invention were used to induce IF in the cells and serum of test animals and the activity of the resultant IF was determined by the methods hereinafter described in Experiment 1. The results shown in Table 1 indicates that the IF inducing activity is positive.

TABLE 1

| | Concentration of sample (μg/ml) | | | |
|---|---|---|---|---|
| | 10 | 1.0 | 0.1 | 0.01 |
| Activity in vitro | >100 | >100 | 94 | <10 |

TABLE 2

| Activity in vivo* | Time of collection of blood after administration (hour) | | | | |
|---|---|---|---|---|---|
| | 0 | 1 | 2 | 4 | 6 |
| Rabbit 1 | <10 | 90 | 240 | 30 | 13 |
| Rabbit 2 | <10 | 25 | 64 | 14 | 10 |

*Dose = 500 μg/ml

Table 2 indicates that the results obtained by the method hereinafter described in Experiment 1 using two rabbits show the activity reaches its maximum 2 hours after administration. It was also confirmed that by the method of Experiment 1, IF was induced in the body of the test animals by the action of the IF inducer of this invention.

(2) Stability of the IF inducer:

Samples (each 1 mg) of the IF inducer of this invention were respectively dissolved in water (each 1 ml) and heated at 100° C. for a given time or at a given temperature for one hour, and was then treated by the method of hereinafter described in Experiment 1 (in vitro method) to obtain the results shown in Tables 3 and 4 indicating a high heat stability of the IF inducer of this invention.

TABLE 3

| Heating temperature (C.°) | Activity at Concentration of sample (μg/ml) | | | |
|---|---|---|---|---|
| | 10 | 1.0 | 0.1 | 0.01 |
| | IF activity | | | |
| Untreated | >100 | >100 | 88 | <10 |
| 37 | >100 | >100 | 88 | <10 |
| 60 | >100 | >100 | 80 | <10 |
| 80 | >100 | >100 | 88 | <10 |
| 100 | >100 | >100 | 85 | <10 |

Heating time: one hour.

TABLE 4

| Heating time (hour) | Activity at Concentration of sample (μg/ml) | | | |
| --- | --- | --- | --- | --- |
| | 10 | 1.0 | 0.1 | 0.01 |
| Untreated | >100 | >100 | 96 | <10 |
| 1 | >100 | >100 | 92 | <10 |
| 4 | >100 | >100 | 98 | <10 |
| 8 | >100 | >100 | 95 | <10 |
| 24 | >100 | >100 | 70 | <10 |

Heating temperature: 100° C.

From the above-mentioned characteristics, it has been found that the active substance of this invention conforms to widely recognized definition of any IF-inducer. The induced IF in animal cell or serum in vitro or in vivo is inactivated with 0.08% trypsin at 37° C. for 2 hours and morover its activity is specific with respect to an animal species and non-specific with respect to a viral species.

In Tables 1-4, the samples used were prepared by the method of Example 1.

It is thus believed that the active substance of this invention is not only a new IF inducer but also a new substance because no such a substance has, to our knowledge, ever been reported in the art. For example, mitogenic agents such as phytohemagglutinin, pokeweed mitogen and cncanavallin A described in the literatures are types of protein having very weak IF-inducing activity which is inactivated on heating at 56° C. for 5 hours, on the contrary to high heat stability and high IF-inducing activity of the active substance of this invention. The known IF inducers isolated from the root of Angelica actiloba Kitagawa is high molecular and its IF-inducing activity is not inactivated on heating at 100° C. for one hour. However, its chemical constituents and infrared absorption spectrum are different from those of the active substance of this invention. The known IF inducer isolated from the peeling of mulberry root contains as main constituent a 1-3 bonded glucose and has a different molecular weight. Moreover, the mitogenic activity which is found in the known IF inducers originating from bactrial endotoxin and higher plants such as Angellica actiloba and mulberry is not found in the IF inducer of this invention.

Various plants of the genus Perilla and variants thereof which may be used as a source of the product of this invention contain, for example, perilla aldehyde, α-pinene, 1-limonene, perilla ketone, naginata ketone, shisonin, p-cumaric acid ester, dihydroperilla alcohol, 1-menthol and the like, all of which are low molecular weight substances and, to our knowledge, have no IF-inducing activity. The physico-chemical characteristics of the known IF inducers [disclosed in U.S. Pat. Nos. 3,583,893; 3,773,924 and 3,884,845 and Japanese Kokai Koho 121919/78] are different from those of the IF inducer of this invention.

According to another feature of this invention, we provide a process for producing an interferon inducer from the plant tissue, comprising extracting the said IF inducer with water from the tissue of a plant selected from the genus Perilla and variants thereof containing the said IF inducer at a temperature from ambient to the boiling point of the extraction mixture for a period sufficient to extract the major portion of the IF inducer present in the tissue, forming a supernatant from the extracted solution, fractionating the supernatant to yield fractions containing a major portion of the IF inducer present in the supernatant, and recovering the IF inducer therefrom.

The plants which may be used for the process of this invention include the plants of the genus Perilla which are annual herbs grown mainly in e.g. India, East Asia and other countries and which are liable to form various variants such as mutants and hybrids naturally or artificially. It has been found that many plants of the genus Perilla and variants thereof may preferably be used for the purpose of this invention. The following plants are merely indicated as examples [*Japanese nomenclature]: Shiso* (P. frutescens Britton var. crispa Dec. f. purpurea Makino); Aojiso* (P. frutescens Britton var. crispa Dec. f. viridis Makino); Katamen-jiso* (P. frutescens Britton var. crispa Dec. f. discolor Makino); Chrimen-jiso* (P. frutescens Britton var. crsipa Dec. f. crispa Makino); Chrimen-aojiso* (P. frutescens Brit. var. crispa Dec. f. viridiscrispa Makino); Toranoo-jiso* (P. frutescens Brit. var. hirtella Makino et Nemoto); Egoma* (P. frutescens Britton); Lemon-egoma* (P. citriodora Nakai and variants thereof.

[The botanical names are designated with reference to "Genshoku Shokubutsu Dai Zukan", vol. I, authored by Murakoshi and Makino and published by Hokuryu-kan, Tokyo (1955), "Yakuyo Shokubutsu Dai Jiten", edited by Kariyone and Kimura and published by Hirokawa Shoten, Tokyo (1974) and "Saishin Wakan Yakuyo Shikubutsu", authored by Kariyone and Kimura and published by Hirokawa Shoten, Tokyo (1978).].

It is known that the plants exemplified above have generally low toxicity, and for example, Shiso, Aojiso Chirimen-jiso and Lomon-egoma are cultured in Japan, China and other countires because their leaves and seeds have been used since long as foodstuffs, Sino-Japanese crude drugs, raw material for production of perfume and the like. Labiatae is a family with many genera containing essential oils such as sage or mint, and to our knowledge, it was not previously known that any plant of Labiatae contains a substance having IF-inducing activity, as reported, e.g. by Keisetsu Otsuka [Kanpo, Geschichte, Theorie und Praxis, 165-189 (1976)], Richard Hyatt [Chinese Herbal Medicine, Ancient Art & Modern Science, 136 (1978)] and John D. Keys [Chinese Herbs, Their Botany, Chemistry and Pharmacodynamics, 256 (1978)].

Although any and all the tissues of Perilla plants may be used for the process of this invention, the leaves and stems are preferred because the seeds contain a weak activity and moreover, additional operation may be neccesary for removing the soil from the root of the plant. Both the leaves and stems contain substantially the same amount of the active substance. The amounts of the active fractions contained in various tissue of a plant are substantially unchanged before and after the flowering period.

For better preservation and extraction, it is preferred to use the dried plant, although it is possible to use the fresh material if desired. The drying method is convenient. If desired, the material may be washed with water before use.

The extraction may preferably effected with water at any convenient temperature, e.g. from ambient to the boiling point of the extraction mixture. As the active substance of this invention is particularly soluble in water under alkaline conditions (e.g. at a pH of 7-10), it is preferred to adjust the pH of water before use, for example, with a suitable buffer solution, sodium hydroxide, potassium hydroxide, ammonium hydroxide and the like. The extraction may be effected over any convenient period of time, usually 1–5 days at room temperature, which may be shortened if the extraction temperature is raised. Thus, for example, the extraction may be effected for a period of time from 30 minutes to 6 hours at 45°–80° C. with or without stirring. In this manner, it is possible to extract a major portion of the active substance contained in the starting material (in some cases, more than 90%). However, the use of an excessively high temperature should be avoided because the quantity of undesired impurities such as e.g. pigments, low molecular weight substances and the like appearing in the extract may thereby increase. It is also possible to add a suitable antiseptic agent to the extracting water. The extraction may be effected continuously or intermittently at any convenient ratio of the extracting water to the raw plant.

It is also possible, if desired to extract the active substance with a hydrophilic organic solvent incapable of dissolving the IF inducer of this invention such as e.g. methanol, ethanol, propanol, butanol, acetone and the like in any convenient amount e.g. 20–80%. In such a case, the extraction time and temperature may be convenient e.g. for 4 hours to 2 days at 40° to 80° C. In such cases, the extraction may be effected by using a hydrophilic organic solvent in spite of the insolubility of the pure product of this invention in such solvents, for example when the extracted solution contains a mixture of complex of substances such as e.g. fatty acids, steroids, proteins, mono- or polysaccharides and the like. Whilst we do not wish to be bound with theoretical considerations, it is believed that extraction using such solvents is made possible by buffer action. However, extraction with water is most advantageous because it is simpler, cheaper and safer in operation.

The residue of the plant tissue is then removed from the extracted solution in conventional manner, for example, by filtration, pressing, centrifugation and the like. After this, undesired impurities such as pigments, low molecular weight substances are removed from the resultant supernatant in order to allow recovery of the active substance of this invention. Preferred methods for this purpose are exemplified as follows.

(A) The supernatant is fractionated by ultrafiltration e.g. using a suitable membrane for retatining substances having a molecular weight of more than 100,000 because the active substance of this invention is present in fractions having a molecular weight of about 100,000 to about 3,000,000 (mainly about 200,000 to about 1,000,000). The ultrafiltration may be effected under suitable pressure, for example, 0.1 to 5 kg/cm$^2$ by using a membrane capable of retaining substances having a molecular weight of more than 100,000 or 200,000. The active fractions are collected and combined, and the combined fractions are freeze-dried to obtain brown powders.

(B) The supernatant is concentrated, if desired, under reduced pressure and is treated with a hydrophilic organic solvent (e.g. methanol, ethanol, propanol, n-butanol, acetone and the like) at a convenient concentration (e.g. 40–70 w/v %) so as to form precipitates containing the active substance. The precipitates are freeze-dried to obtain brown powders.

(C) Instead of the organic solvent, it is possible to add to the supernatant an ammonium salt (e.g. ammonium chloride, ammonium sulfate, cetylmethylammoniumbromide and the like) or an inorganic metalic salt (e.g. zinc chloride, copper chloride and the like) at a convenient concentration (e.g. 20 to 50 w/v %) so as to form precipitates which are then desalted and freeze-dried to obtain brown powders.

It is possible to recover the major portion of the active substance contained in the starting material (in some cases, more than 90%). However, the quantity of impurities contained in the crude powder is lowest in the case of method (A), and also method (A) may be effected simply. Moreover, it has been confirmed that any significant side effect may be avoided even when a large amount of the crude powder obtained by (A) is orally administered to humans and animals and thus this crude powder may be used for oral administration without further purification.

If desired, the crude powder thus obtained may further be purified, for example, by column chromatography using a suitable agent for gel filtration or an ion exchanger. In the former case, the elution may be effected with water, although it is possible to use a suitable buffer solution. In the latter case, the elution may be effected with a suitable buffer solution. Preferable agents for gel filtration are exemplified by Sephadex G-50 to G-200, Sepharose 2B to 6B, Sephacryl S-200 or S-300 (commercial products of Pharmacia Fine Chemicals AB., Sweden), Bio-Gel P-30 to P-300, Bio-Gel A (commercial products of Bio-Rad Laboratories Ltd., U.S.A.), Sagavac (commercial by QAE-Sephadex A-25 and A-50 (Cl$^-$ form), CM-Sephadex C-25 and C-50 (Na$^+$ form), SP-Sephadex C-25 and C-50 (Na$^+$ form), DEAE-Sephacel (Cl$^-$ form), DEAE-Sepharose CL-6B (Cl$^-$ form), CM-Sepharose CL-6B (Na$^+$ form) (commercial products of Pharmacia Fine Chemicals AB., Sweden) and the like. It is also possible to use a suitable anion or cation exchange cellulose for the purification. The product thus-obtained may contain certain impurities, although its IF-inducing activity is sufficient for practical purposes. If desired, the amounts of impurities may further be reduced by combining these treatments.

It is apparent moreover that the process of this invention may be applied not only to Labiatae but also to all the higher plants such as Tracheophyta e.g. Mono- or Dicotyleodoneae when they contains a substance having IF-inducing activity and water-solubility.

According to a further feature of this invention, there is provided a process for inducing an IF in the body or cells of human or animal, which comprises administering an effective amount of the IF inducer of this invention to a human or IF-inducing animal.

The active substance of this invention may be used without any toxic trouble which is inherent to various known IF inducers such as e.g. polyI:C, endotoxin and the like. Moreover it has also been found that when administered to humans, the activity of the IF inducer of this invention is superior to those of the known IF inducers. The IF inducer of this invention is capable of not only affording a high antiviral activity but also enhancing anti-tumour activity and overall physiological activities. It is thus possible to use the IF inducer of this invention not only for the prevention and curing of various virally caused diseases of various vetebrates such as, for example, humans, mammals (e.g. cattle, horse, pig etc.), birds (e.g. fowl, duck etc.), fishes (e.g. rainbow trout etc.) and the like but also as anti-tumour agent, agent for improving overall healthy conditions for humans and animals.

The active substance of this invention may be administered e.g. by intravenous or intraperitoneal administration, intestinal or oral administration, spraying and the like.

In the case of intravenous administration, it may be possible to administer the active substance at a dose of 0.001 to 100 mg/kg/day, calculated as the final product. However, such a dose may vary, depending upon, for example, the type, age and weight of the host and various other conditions, among which the response of the host to IF induction and the purpose of the administration are most important. The active substance of this invention may preferably be administered to animals, for example, at a daily dose of 0.01 to 10 mg/kg (iv.) or 0.1 to 10 mg/kg (ip.) and to humans at a daily dose of 0.01 to 1.0 mg/kg (ip.) by injection. In the case of oral administration, it is possible to use, for example, more than about 10 times of the dose for intravenous administration. When the administration is effected topically or in a shorter period of time, a larger amount of the active substance may be used. When the dose is excessively small, it may be difficult to induce IF in the body or cells of the host. However, the use of an excessively large amount of the active substance of this invention may, in general, give rise to no serious side effect because its toxicity is extremely low.

It has also been found that when a suitable amount of any IF is administered to a host, followed by administering the active substance of this invention, the activity of the IF induced by the active substance of this invention may significantly be enhanced and for example about 3-10 folds activity may be obtained thereby. Moreover, it is possible in this manner to enhance considerably the response of the host to IF induction and also to extend the effective period of time of the IF induced.

The following samples were used in the following tests:

Sample A: The crude powder obtained by ultrafiltration by the method of Example 1 and freeze-dried.

Sample B: The finally purified product by the method of Example 1.

Sample C: The finally purified product by the method of Example 2.

As test animals, rabbits (same type as that used in hereinafter described Experiment 1), mice (weight 25±1 g, ddy-strain, 6 weeks old) and fowls (weight about 230 g, White Leghorn, 30 days old) were used.

(A) IF Induction and Determination of IF Activity (I) In vitro Method

A spleen cell suspension ($10^7$ cells/ml) was prepared by the method of hereinafter described Experiment 1 using an Eagle MEM medium (commercial product of Nissui Seiyaku K.K., Tokyo) containing a 10% calf serum (which was replaced by a 10% fetal cattle serum in the cases of human tests), each of which fraction (1 ml) was added with a given concentration of the sample of the active substance and incubated at a given temperature. The cultured liquor was centrifuged to separate a supernatant which was used for determining the IF activity induced. In the case of humans, the fresh spleen was collected from a man (adult deceased by external wounds) and used for the preparation of a leucocytes suspension on each occasion, and also blood was collected from the vein at the upper arm of a man (adult), from which the serum was separated to use for the preparation of a serum suspension on each occasion.

The IF activities were determined by using the cells shown in Table 5 in a similar manner to that hereinafter described in Experiment 1.

TABLE 5

| | IF induction in vitro | | |
|---|---|---|---|
| | I | II | III |
| Rabbit | 3 | 25 | RK-13 |
| Mouse | 30 | 37 | L |
| Human spleen | 2 | 25 | FL |
| Human leucocytes | 5 | 37 | FL |
| Fowl (White Leghron) | 5 | 37 | Fibroblast |

I: Numbers in each group
II: Cultured for 24 hours at a temperature of (°C.)
III: Cells used for determination The results are shown in Table 6.

TABLE 6

| | | IF activity in vitro | | | | | Control* |
|---|---|---|---|---|---|---|---|
| | | Concentration (μg/ml) | | | | | |
| | Sample | 100 | 10 | 1 | 0.1 | 0.01 | 1.0 |
| Rabbit | A | 200 | 255 | 90 | <5 | <5 | |
| | B | 240 | 270 | 250 | 140 | 40 | 220 |
| | C | 260 | 300 | 285 | 165 | 45 | |
| Mouse | A | 65 | 85 | 30 | 10 | <5 | |
| | B | 195 | 225 | 140 | 75 | 20 | 120 |
| | C | 210 | 250 | 155 | 80 | 10 | |
| Human | A | 30 | 35 | 12 | <5 | <5 | |
| (spleen) | B | 34 | 40 | 20 | 8 | <5 | <5 |
| | C | 35 | 38 | 21 | 10 | <5 | |
| (leucocytes) | B | 30 | 20 | 12 | <5 | | |
| Fowl | A | 25 | 12 | <5 | | | |
| | B | 74 | 48 | 10 | <5 | | |
| | C | 80 | 52 | 12 | <5 | | |

*Poly I:C (II) In vivo Method:

(1) Rabbit

Table 2 shows the IF activities induced in rabbits by the method hereinafter described in Experiment 1.

TABLE 2

| | Used sample: sample B* | | | | |
|---|---|---|---|---|---|
| | Time of collection of blood after administration of sample | | | | |
| IF activity (in vitro) | 0 | 1 | 2 | 4 | 6(hour) |
| Rabbit 1 | <10 | 90 | 240 | 30 | 13 |
| Rabbit 2 | <10 | 25 | 64 | 14 | 10 |

*Dose: 500 μg/ml

Similar treatments were repeated by changing the dose of the sample stepwise within a range of 4 to 0.004 mg/kg, and it was found that the IF activity induced in the serum reached its maximum 2 hours after administration. Also, the maxium was observed about 12 to 15 hours after oral administration.

(2) Mouse

Mice (each group consisting of 10 mice) were used as test animals and treated as follows.

(a) Each 0.1 ml of a physiological solution of sodium chloride containing a given amount of sample B shown in Table 4 was injected into the vein at the tail of each mouse which was then allowed to stand for 1, 2, 3 or 5 hours, or (b) Each 0.2 ml of a physiological solution of sodium chloride containing a given amount of sample B shown in Table 4 was administered (ip) to each of the mice which was then allowed to stand for 2, 4 or 6 hours, or (c) Water (0.2 ml) containing a given amount of sample B shown in Table 4 was orally administered to each mouse which was then allowed to stand for 2.5, 5, 7.5 or 10 hours.

On each occasion, the test animal was then sacrificed by cardic puncture. Blood was collected from each mouse and used to prepare the serum. The IF activity induced was determined in a similar manner to that described above. It was observed that the IF activity reached its maximum about 2-3 hours in the case (a), about 2-4 hours in the case (b) and about 5-8 hours in the case (c), after administration. Table 7 indicates the maximum IF activities (mean value). A similar tendency was also found when the same treatments were repeated by using sample A instead of sample B.

TABLE 7

| Maximum IF activity in vivo (mouse) | | | |
|---|---|---|---|
| Concentration (mg/kg) | Intravenous | Ip. | Oral |
| 4000 | | | 33 |
| 400 | | | 22 |
| 40 | 730 | 280 | 20 |
| 4 | 200 | 85 | <5 |
| 0.4 | 175 | 53 | |
| 0.04 | 64 | 20 | |
| 0.004 | 25 | <5 | |
| Untreated | <5 | <5 | <5 |

(3) Humans

Each 200 mg of sample B was orally administered to each of five men (adults, healthy). Blood was collected from the vein at the arm of each volunteer after 13 hours from administration and used for the preparation of the serum which was then treated in a similar manner to that described above to determine the IF activity of about 15 units (mean value).

(4) Fowl

Fowls (each group consisting of 10 chickens) were used as test animals. A physiological solution of sodium chloride (each 0.2 ml) containing sample B (4 mg/kg) was administered into the vein under the wing of each animal. After 2 hours on each occasion, the fowl was sacrificed by cardic puncture. Similarly, blood was collected for use to determine that the IF activity induced in the serum was about 30 units.

(B) Protection Against Viral Infections (1) Mouse (Vaccinia Virus)

Mice (each group consisting of 20 female) were used as test animals, to each of which was administered a physiological solution of sodium chloride (each 0.2 ml) containing a given amount of the sampel shown in Table 5 intravenously, intraperitoneally or orally. After 24 hours, each mouse was infected with Vaccinia virus at a dose of of 30 PFD [1 PFD denotes an amount of the virus capable of forming the pocks at the tails of 50% of the mice used] contained in 0.1 ml of a physiological sodium chloride solution by injecting into the vein at the tail. For 9 days after this, the numbers of the pocks formed at the tail were compared with the corresponding numbers of the pocks found in the untreated mice (39.8 in average) to determine the inhibition ratio. A ratio of more than 50% was evaluated as an effective ratio. The results are shown in Table 8.

TABLE 8

| Method of administration | Concentration (mg/kg) | Inhibition ratio (%) Sample | | |
|---|---|---|---|---|
| | | A | B | C |
| Intravenous | 40 | 100 | 100 | 100 |
| | 4 | 93 | 100 | 100 |
| | 0.4 | 72 | 100 | 100 |
| | 0.04 | 61 | 89 | 90 |
| | 0.004 | 38 | 67 | 65 |
| Ip | 40 | 87 | 100 | 100 |
| | 4 | 68 | 100 | 100 |
| | 0.4 | 45 | 93 | 95 |
| | 0.04 | 31 | 75 | 75 |
| | 0.004 | 18 | 45 | 42 |
| Oral | 4000 | 53 | 70 | 67 |
| | 2000 | 42 | 66 | 65 |
| | 400 | 28 | 55 | 54 |

(2) Mouse: (Herpes Simplex Virus)

Similar treatments to those described above were repeated, but Vaccinia virus was replaced by Herpes Simplex virus. The sample was administered intravenously, orally or ip to the test animals in a similar manner to that hereinbefore described in (B,1), followed by intraperitoneal infection of the virus. The results were observed for 30 days after infection to determine the average survival days which were compared with the corresponding days of untreated group. A significant survival effect was found.

(3) Rabbit (Vaccinia Virus)

(a) Rabbits (each group consisting of 5 rabbits) were used. A physiological sodium chloride solution (each 0.1 ml) containing a given amount of sample A was injected on each occasion under the skin at the back of the rabbit and 24 hours after this, Vaccinia virus (1 $ID_{50}$ which denotes an amount of the virus capable of forming at least one pock of more than $6 \times 6$ mm in size under the skin of 50% of the test rabbits) in 0.1 ml of a physiological sodium chloride solution was injected into the same site in a similar manner to that used for administration of the sample. 7 days after this, the numbers of the pocks were counted and compared with the corresponding numbers found on the untreated rabbits. The concentration of the sample was stepwise changed from 0.02 to 200 μg/kg, and it was found that a dose of more than 2 μg/kg gave a 100% inhibition.

(b) A similar treatment to that described in (a) was effected except sample A was divided into 5 equal parts (100 mg/day) and administered to the rabbit on each occasion on the 1st, 3rd, 4th, 6th and 8th days (500 mg/kg in total). The virus was divided into 2 parts (10 and 100 $ID_{50}$) and respectively infected to each rabbit on the 5th day. On the 12th day, no pock was found at the nack of each rabbit infected with 10 $ID_{50}$ virus and weak pocks were found at the back of each rabbit infected with 100 $ID_{50}$ virus. In the latter case, 2 weeks after the infection, the pocks disappeared completely.

(C) Anti-Tumour Effect (Mouse)

(1) Ehrlich Ascites Tumour

Mice (each group consisting of 15 mice) were used as test animals. A sterilized water (each 0.2 ml) containing Ehrlich ascites tumour cells (each $2.5 \times 10^6$) was transplanted into each animal by injection (ip.). 24 hours after this, a given amount of sample B in sterilized water (each 0.2 ml) was given to each animal. The administration was effected once daily at a dose of 0.2, 1.0 or 5 mg/kg/day (ip.) or 40, 200 or 1000 mg/kg/day (orally) and continued for 14 days. By administration at a dose of 1 or 5 mg/kg/day (ip.), one half of the treated mice were still alive and moreover completely cured 60 days after the transplantation. All untreated mice deceased on or before the 29th day after the transplantation. The results are shown in Table 9.

TABLE 9

| Dose | Median survival days | Increased life spun (%) |
|---|---|---|
| 1 mg/kg/day(ip.) | >60 | >122 |
| Untreated | 27 | — |

A similar effect was observed when 5 equal parts (each 1.0 mg/kg) of sample B were administered (ip) to the mice at an interval of 3 days. The result obtained by continuation of oral administration of sample B (400 or 1000 mg/kg/day) for 14 days was not superior to the result obtained by the abdominal administration.

(2) S-180 Sarcoma Solid Tumour

S-180 Sarcoma solid tumour cells ($1 \times 10^5$ cells) were added to a sterilized water (0.2 ml). Each mixture was transplanted to each test mouse (each group consisting of 15 mice) under the skin at the armpit. Samples of the active substance of this invention were administered to the animals in a similar manner to that described above. When a dose of 1 mg/kg/day (ip.) was administered to each of the test animals, the tumours of 5 mice were reduced to about $\frac{1}{2}-\frac{1}{3}$ in size 40 days after administration and 3 mice were completely cured 60 days after the administration. By oral administration at a dose of 1000 mg/kg/day/mouse, 6 mice were alive 60 days after the beginning and their tumours were reduced to about $\frac{1}{3}$ in size. 60 days after this, 3 mice were completely cured. 35 days after the transplantation, no control mouse was alive.

(D) Combined Use of IF and IF Inducer (Priming Effect)

(1) A suspension containing lymphoid cells of rabbits ($10^7$ cells/ml) was prepared by the method of hereinafter described Experiment 1 and was added with rabbit IF (30 unit/ml). The mixture was treated at 37° C. for 6 hours and was then centrifuged to remove the IF. Then an Eagle MEM medium (1 ml) and sample B were added to the cells and its activity was determined with simultaneous change of the amount of sample B from $10^{-3}$ to $10^{-7}$ mg/ml. It was found that the activity of the induced IF raised to about 3-10 folds and also the response of the cells was significantly improved.

(2) By the method of hereinbefore described (D,1), a suspension of human spleen cells ($10^7$ cells/ml) was prepared and treated with human IF (100 unit/ml). The activity of the IF induced raised to about 3-10 folds and also the response of the cells was significantly improved.

(3) Rabbits (each group consisting of 5 rabbits) were administered with rabbit IF ($10^6$ unit) intravenously. 6 hours after this, sample B was given to each rabbit by the method of hereinbefore described (A,II,1). It was found that the IF activity induced in the serum raised to about 3-6 folds and the period of time of IF induction was also extended.

(4) Each of 5 rabbits was administered (ip) with rabbit IF ($10^6$ units) and after 24 hours, an infection test was effected in a similar manner to that described in (B,3,b).

After 12 days from the infection with the virus at a dose of 100 ID$_{50}$, no pock was formed at the back of each treated rabbit.

(E) Toxicity (1) Acute Toxicity

A physiological sodium chloride solution containing a given amount of sample B was administered to each of the test mice (each group consisting of 20 mice; male and female) and test rats (each group consisting of 20 rats; weight about 95 g; SPF strain; 6 weeks old; male and female) to obtain the LD$_{50}$ values shown in Table 10. No significant difference was found between male and female.

TABLE 10

| | Acute toxicity (LD$_{50}$) | | | |
|---|---|---|---|---|
| | Concentration of sample (g/kg) | | | |
| Animal | Subcutaneous | Ip | Iv | Oral |
| Mouse | >2 | 0.56 | 0.45 | 4 |
| Rat | >1 | 0.6 | 0.52 | >2.8 |

(2) Subacute Toxicity

Rats (weight about 95 g; SPF-SD strain; 6 weeks old; each group consisting of 20 rats) were used as test animals. Sample A was divided into fractions (0.35, 0.7, 1.4 and 2.8 g/kg), each of which was added to each sterilized water (from 0.25 to 0.5 ml), and a given amount of the sample was daily administered to the test animals compulsively by using a canule. The administration was continued for 3 months. In comparison with the untreated animals, the healthy conditions of the test animals were improved throughout the test period and their body weights increased at a remarkably high ratio. All animals were dissected after the end of 3 months and investigated pathologically. However, it was difficult to determine the subacute toxicity reasonably because no significant change was observed pathologically.

(b) Five healthy men (adults) were administered orally with Sample A (200 mg/day) and the administration was continued for 10 days. As a result, no significant side effect was observed.

For the purpose of administering the active substance of this invention to humans and animals with good results, there is provided a pharmaceutical composition, which comprises as active ingredient an effective amount of the active substance of this invention as hereinbefore defined, in association with a pharmaceutical carrier or excipient.

The composition may be any and all forms adapted to oral, rectal, perenteral, percutaneous, intramucous administration and the like. Thus, for example, the composition may be solid or liquid for oral administeration and may take the forms of powders, syrups, capsules, granules, emulsions, suspensions, drops and the like. Such composition comprises carrier or excipient conventionally used in the pharmaceutical art. Thus, for example, suitable tabletting excipients include lactose, potato and soluble starch and magnesium stearate, and for parenteral administration, the carrier may be a steril water, physiological solution of sodium chloride, armond oil and the like, which may be put in an ampule or may be added to the active substance before use.

The composition may, if desired, further comprises, for example, bonding agents, stabilizing agents, emulsifiers, suspending agents, dispersing agents, lublicants, antiseptic agents, fillers and the like conventionally used in the pharmaceutical art. Such composition comprises carrier or excipient conventionally used in the pharmaceutical art. Thus, for example, suitable tabletting excipients include lactose, potato and soluble starches and magnesium stearate and for parenteral administration, the carrier may be a sterile water, physiological solution of sodium chloride, armond oil and the like, which may be put in an ampule or may be added to the active substance before use.

The composition may, if desired, further comprise, for example, bonding agents, stabilizing agents, emulsifiers, suspending agents, dispersing agents, lublicants, antiseptic agents, fillers and the like conventionally used in the pharmaceutical art.

For practical purpose, the composition may be formulated, for example, as buccals, troches, eye drops, suppositories and the like for intramucous administration, solutions, oils, suspensions and the like for injection agents, inhalants, sprays and the like for inhalational administration and ointments, plasters, liniments, bathes, sprays and the like for external administration.

Advantageously, the composition may be formulated as dosage units, each unit being adapted to supply a fixed dose of active ingredient. Suitable dosage unit forms are, for example, tablets, coated tablets, ampules, capsules, suppositories and the like.

The amount of the active ingredient preferably contained in such dosage unit forms may, for example, be within a range of from about 4 to about 10 for oral administration, about 2–3 for subcutaneous administration, about 1.5–3 for intramuscular administration, about 2–4 for baccals and troches and about 5–10 for suppositories, calculated on the basis of the preferred amount for intravenous injection.

The compositions are exemplified as follows.

| (1) Parenteral injection: | |
|---|---|
| Physiological solution of NaCl | 1.0 ml |
| Sample B | 0.01 g |
| packed and sealed in a 2 ml ampule under sterilzed conditions. | |
| (2) Troch: | |
| White sugar | 1 g |
| Sample B | 0.05 g |
| Starch | 0.05 g |
| (3) Suppository: | |
| Polyethylene glycol 400 | 0.8 g |
| Liquid polyethylene glycol 1500 | 0.2 g |
| Sample A | 0.2 g |
| (4) Syrup: | |
| CMC-Na | 0.2 g |
| Simple syrup | 20 g |
| Ethylparaffin | 0.04 g |
| Sample B | 0.1 g |
| (5) Ointment: | |
| Purified lanolin | 5 g |
| Yellow wax | 5 g |
| White vaselin | 87 g |
| Sample B | 3 g |
| (6) Liniment: | |
| Potassium hydroxide | 0.3 g |
| Glycerin | 20 ml |
| Ethanol | 25 ml |
| Sample B | 2.5 g |
| Make-up water | to 100 ml |

DRAWINGS

FIG. 1 and 2 show respectively the ultraviolet and infrared absorption spectra of the active substance of this invention.

PREFERRED EMBODIMENTS

The following non-limiting examples illustrate the preparation of the active substance of this invention.

EXAMPLE 1

Dried leaves of *Perilla frutescens* Britton var. crispa Dec. f. purpurea Makino (known in Japan as Shiso) (1 kg) were washed with water and allowed to stand in water (20 l) at room temperatureor 3 days to effect extraction, followed by centrifugation (6000 r.p.m.) for 20 minutes to remove the residue which was washed with water (each 5 l). The washing liquid was combined with the supernatant, and the combined solutions were fractionated by ultrafiltration using an ultrafilter (Model UD-6, commercial product of Bio Engineering K.K., Tokyo) with a UK 200 membrane (commercial product of Toyo Roshi K.K., Tokyo) for retaining substances having a molecular weight of 200,000 at a pressure of 3 kg/cm$^2$ to give a resiude which was then freeze-dried to obtain a brown powder (8.813 g). This powder (1.5 g) was dissolved in water (5 ml) and transferred to a column (4.5×70 cm) packed with Sephadex G-200 (an agent for gel filtration, commercial product of Pharmacia Fine Chemicals AB., Sweden). The elution was effected with water (600 ml) and the effluent was divided into fractions (each 3 ml). Fraction Nos. 27–50 were collected and combined and the combined fractions were freeze-dried to obtain a whitish powder (117 mg).

For further purification, this powder (100 mg) was dissolved in a 0.1 M tris-HCl buffer solution (5 ml; pH 7.0; I=0.01) and transferred to a column (2.5×70 cm) packed with DEAE-Sephadex A-50 (an iron exchanger, commercial product of Pharmacia Fine Chemicals AB., Sweden). The elution was effected with a 0.1 M tris-HCl buffer solution (300 ml; pH 9.0; containing 0.5 M NaCl). The effluent was divided into fractions (each 3 ml) and Fraction Nos. 15–25 were collected and combined, and the combined fractions were freeze-dried to obtain a whitish powder (58.9 mg) containing smaller amounts of impurities and having a sub-whitish powder. The physico-chemical characteristics of the final product are as hereinbefore described, and its high purity was confirmed by ultracentrifugation and electrophoresis.

For comparison purpose, the IF inducting activities of the substances obtained by respective process steps in this example were determined by the method hereinafter described in Experiment 1 (in vitro) to give the following results.

TABLE 11

| Step | Concentration of sample ($\mu$g/ml) | | |
|---|---|---|---|
| | 10 | 1.0 | 0.1 |
| (a) Extraction | 90 | <10 | <10 |
| (b) Ultrafiltration | >100 | 85 | <10 |
| (c) Gel filtration | >100 | >100 | 94 |
| (d) Ion exchange treatment (final product) | >100 | >100 | >100 |

EXAMPLE 2

A similar treatemnt to that described in Example 1 was effected with the exception that *Perilla frutescens* Britton (known in Japan as Egoma) was extracted by allowing the leaves (1 kg) to stand in water at room temperature for 2 hours and adding to the water 1 N sodium hydroxide to adjust the pH to 8.5, followed by further extraction at 65° C. for 2 hours. The physico-chemical characteristics of the final product (54.5 mg) were substantially the same as those of the final product of Example 1.

EXAMPLES 3–8

The leaves, stems and seeds or dried *Perilla frutescens* Britton var. crsipa Dec. f. purpurea Makino (Shiso*); *P. frutescens* Britton (Egoma*); *P. frutescens* Brit. var. crispa Dec. f. viridis Makino (Aojiso*); *P. frutescens* Brit. var. crispa Dec. f. discolor Makino (Katamen-jiso*); *P. frutescens* Brit. var. crispa Dec. f. crispa Makino (Chirimen-Jiso*): *P. frutescens* Britton var. crispa Dec. f. viridis-crispa Makino (Chrimen-aojiso*); *P. furtescens* Brit. var. hirtella Makino et Nemoto (Toranoojiso*) and *P. citriodora* Nakai (Lemon-egoma*) [*Japanese nomenclature] were separately treated in a similar manner to that described in Example 1. The physico-chemical characteristics of their final products were substantially the same as those of the final product of Example 1.

an Eagle MEM medium (commercial product of Nissui Seiyaku K.K., Tokyo) containing a 10% calf serum. This suspension was divided into fractions (each 1 ml), and 4 fractions were respectively added with 10, 1.0, 0.1 and 0.01 μg/ml of an active substance prepared by the method of Example 1, which was incubated at 25° C. for 24 hours, followed by centrifugation to obtain each supernatant which was then used to determine the activity of the IF induced.

(b) IF Induction in vivo

An aqueous solution (2 ml) of the active substance prepared by the method of Example 1 (500 μg/ml) was injected into the auticular vein of a rabbit (weight about 1 kg; New Zealand White; SPF). 1, 2 4 and 6 hours after this, a 2 ml sample of blood was removed from the rabbit on each occasion and used to prepare the serum used to determine the IF activity.

(c) Determination of IF Activity

In both (a) and (b), the activity of the IF induced was determined in reliance with the reduction ratio of plaques in the following manner.

A monolayer culture of the lined cells RK-13 of rabbit was put in a dish and added with a predetermined amount of the solution obtained by the method (a) or (b) (suitably diluted). The culture was incubated at 37° C. overnight of Vesicular stomatitis virus was then added and used as the challenge virus. The IF activity is indi-

TABLE 12

No. — Example Number; A — Seed; B — Stem; C — Leaf

| No. | Plant | Tissue | Activity at (concentration of sample) | | |
|---|---|---|---|---|---|
| | | | 10 | 1.0 | 0.1 μg/ml |
| 1. | Shiso* (*Perilla frutescens* Britton var. *crispa* Dec. f. *purpurea* Makino) | A | 70 | <10 | <10 |
| | | B | >100 | >100 | 90 |
| | | C | >100 | >100 | 92 |
| 2. | Egoma* (*P. frutescens* Brit.) | A | 40 | <10 | <10 |
| | | B | >100 | >100 | 90 |
| | | C | >100 | >100 | 85 |
| 3. | Aojiso* (*P. frutescens* Brit. var. *crispa* Dec. f. *viridis* Makino) | A | 60 | <10 | <10 |
| | | B | >100 | >100 | 95 |
| | | C | >100 | >100 | 90 |
| 4. | Katamen-jiso* (*P. frutescens* Brit. var. *crispa* Dec. f. *discolor* Makino) | A | 65 | <10 | <10 |
| | | B | >100 | >100 | 90 |
| | | C | >100 | >100 | 84 |
| 5. | Chirimen-Jiso* (*P. frutescens* Brit. var. *crispa* Dec. f. *crispa* Makino) | A | 50 | <10 | <10 |
| | | B | >100 | >100 | 90 |
| | | C | >100 | >100 | 80 |
| 6. | Chirimen-aojiso* (*P. frutescens* Brit. var. *crispa* Dec. f. *viridis-crispa* Makino) | A | 70 | <10 | <10 |
| | | B | >100 | >100 | 85 |
| | | C | >100 | >100 | 80 |
| 7. | Toranoo-jiso* (*P. frutescens* Brit. var. *hirtella* Makino et Nemoto) | A | 50 | <10 | <10 |
| | | B | >100 | >100 | 70 |
| | | C | >100 | >100 | 70 |
| 8. | Lemon-egoma* (*P. citriodora* Nagai) | A | 50 | <10 | <10 |
| | | B | >100 | >100 | 70 |
| | | C | >100 | >100 | 65 |

*By Japanese nomenclature

EXPERIMENT 1

Determination of IF induced by IF inducer and IF assay: [Reference: Y. Kojima's report in Kitasato Arch. Med., 43:35 (1970)]

(a) IF Induction in vitro

A rabbit (weight about 1 kg; New Zealand White; SPF) was sacrificed by cardic puncture and its spleen, bone marrow and lymph node cells were collected and combined together, from which a cell suspension containing the mixed cells ($10^7$ cells/ml) was prepared using cated by the reduction ratio of plaques and the unit of the IF activity is expressed by the reciprocal number of the highest dilution of the sampel required for reducing the numbers of plaques to 50%.

EXPERIMENT 2

Definition of IF Inducer

The active substance of this invention represents an IF inducer because the samples prepared by the methods (a) and (b) are capable of inhibiting the growth of Vesicular stomatitis virus and Vaccinia virus in the lined RK-13 cells of rabbits of the same animal species, but do not inhibit the growth of Vesicular stomatitis virus in L cells of mice i.e. of a different animal species, and moreover, their IF activities are inactivated by treating with 0.08% trypsin at 37° C. for 2 hours. It has also been found that the IF induced by the active substance of this invention is stable when dialized against a pH 2 buffer solution at 5° F. for 2 days, unstable on heating at 60° C. for 2 hours, gives no precipitate by centrifugation at 100,000 xg for 2 hours and is non-toxic against the cells at the minimum virus-inhibitory level. The IF induced by the active substance of this invention may be classified into Type-I IF and consists of a complex of α- and β-types. Also it has been observed that IF is induced when the active substance of this invention is used, for example, for treating the cells of bone marrow, lymph node, spleen and the like in vitro or injected into the body of animals, but no IF is induced when applied to treat the primary or continuous cell cultures which are known to induce IF by viral infection or treating with poly I:poly C.

EXPERIMENT 3

In Example 1, the elctrophoresis was effected at 4° C. in conventional manner using a commercially available device (Model AE-2, product of Toyo Kaguku Sangyo K.K., Tokyo), a polyacrylamide gel plate (thickness 3 mm) and a 0.3 M boric acid buffer (pH 8.4). The resultant single band indicated that the rest sample had a high putity.

EXPERIMENT 4

Determination of Specific IF Inducing Activity (A) In a similar manner to that described in Example 1, dried leaves of Perilla frutescent Britton var. crispa Dec. f. purpurea Makino (1 kg) were extracted with water (20 l) to give an extracted solution (dry weight: 92.892 g) which was subjected to ultrafiltration using a membrane (UK 200) for fractionating substances having a molecular weight of more than 200,000 to give a residue and filtrate. The residue was freeze-dried to give a crude powder (dry weight: 8,813 g) referred to as Fraction No. 1. Similarly, the filtrate was treated by using a membrane (UK 10) for fractionating substances having a molecular weight of more than 10,000 to give a residue and filtrate, both of which were freeze-dried respectively to give solid substances referred to as Fraction Nos. II (dry weight: 10.751 g) and III (dry weight: 71.328 g).

The IF activities induced by Fraction Nos. I, II and III were individually determined by the methods of Experiment 1 to find out that Fraction No. I was active and no or little activity was present in II and III.

Subsequently, Fraction No. 1 (1.5 g) was dissolved in water (5 ml) and applied to a column (4.5×70 cm) packed with Sephadex G-200 (commercial product of Pharmacia Fine Chemicals AB., Sweden). Gel filtration was effected with water (600 ml) and the effluent was divided into fractions (each 3 ml). 0.5 ml of each fraction was used to develop the color by the phenol/sulfuric acid method and the absorption at 485 mμ was determined by using a Hitachi Spectrophotometer (Model 40-100, commercial product of Hitachi Limited., Tokyo). In reliance upon the peaks observed, these fractions were classified and combined to give 7 groups. Each group was freeze-dried and used for determining the IF activity induced in vitro by the method of Experiment 1. The results are shown in the following table, in which Fraction No. I-1 corresponds to Fraction Nos. 27–50 described in Example 1.

TABLE 13

A: Fraction No. (molecular weight)
B: Yield (%) [100% = dry weight of the starting material]
C: Recovery ratio (%)
D: IF activity in vitro at a concentration of μg/ml

| A | B (%) | C (%) | D(μg/ml) 10 | 1.0 | 0.1 |
|---|---|---|---|---|---|
| After ultrafiltration | | | | | |
| All extracts | 9.29 | | 90 | <10 | <10 |
| I (>200,000) | 0.88 | 9.68 | >100 | 85 | <10 |
| II (200,000–10,000) | 1.08 | 11.88 | 30 | <10 | <10 |
| III (<10,000) | 7.13 | 78.44 | <10 | <10 | <10 |
| After gel filtration | | | | | |
| I-1 | 0.085 | 9.66 | >100 | >100 | 94 |
| I-2 | 0.055 | 6.25 | 60 | <10 | <10 |
| I-3 | 0.017 | 1.93 | <10 | <10 | <10 |
| I-4 | 0.022 | 2.50 | <10 | <10 | <10 |
| I-5 | 0.595 | 67.61 | <10 | <10 | <10 |
| I-6 | 0.020 | 2.27 | <10 | <10 | <10 |
| I-7 | 0.086 | 9.77 | <10 | <10 | <10 |

(B) In a similar manner to that described in Example 1, dried leaves of Perilla frutescens Britton var. crispa Dec. f. purpurea Makino (50 g) were extracted with water (1000 ml) at room temperature for two hours, heated at 65° C. for one hour, adjusted to pH 8.5 with addition of 1 N NaOH solution (3 ml), heated at 65° C. for two hours, cooled to room temperature and centrifuged for 30 minutes (7000 r.p.m.) to remove the residue from the supernatant. The residue was washed twice with water (each 200 ml) and the washing liquid was combined with the supernatant. The combined solutions (dry weight 7.49 g) were subjected to ultrafiltration using a membrane (UK-200) capable of fractionating substances having a molecular weight of more than 200,000 to give a filtrate and residue. The residue was freeze-dried to obtain a crude powder (dry weight 0.506 g) which was then freeze-dried to obtain a sub-0.506 g) referred to as Fraction I which was then subjected to gel filtration and used to determine the IF activity by the method of Experiment 1. Separately the filtrate was treated similarly by using a membrane (UK-10, commercial product of Toyo Roshi K.K., Tokyo) for fractinating substances having a molecular weight of more than 10,000 to give a residue and filtrate, both of which were freeze-dried to give substances respectively referred to as Fractions II (dry weight 0.042 g) and III (dry weight 6.843 g). The IF activities induced by these fractions were also determined by the method of Experiment 1. The results are shown in Table 14.

TABLE 14

| Fraction (molecular weight) | Yield (%)* | Recovery ratio (%) | IF activity in vitro at a concentration of 10 | 1.0 | 0.1 μg/ml |
|---|---|---|---|---|---|
| All extracts | 14.98 | | 80 | <10 | <10 |
| I (>200,000) | 1.01 | 6.83 | >100 | 70 | <10 |
| II (200,000–10,000) | 0.08 | 0.54 | 30 | <10 | <10 |
| III (<10,000) | 13.69 | 92.63 | <10 | <10 | <10 |

*100% = dry weight of starting material (C) From (A) and (B), it is apparent that the IF-inducing activity is most prevalent in the fraction having a molecular weight of more than 200,000 and that impurities contained in the extracted solution were almost completely removed by ultrafiltration and gel filtration (more than 98%). The amounts of impurities were further reduced by the following ion exchange treatment as described in Example 1 and an increase of about 10% of the specific activity was observed.

We claim:

1. A process for producing a water soluble interferon inducer having a high molecular weight from a plant tissue, comprising extracting said interferon inducer with water from the tissue of a plant selected from the plants of the genus Perilla containing said interferon inducer at a temperature from ambient to the boiling point of the extraction mixture for a period of up to 5 days to extract said interferon inducer present in said tissue, forming a supernatant from the extracted solution, fractionating the supernatant to yield fractions containing the major portion of said interferon inducer in the supernatant and recovering said interferon therefrom.

2. The process of claim 1, wherein said interferon inducer has a molecular weight of from about 100,000 to 3,000,000.

3. The process of claim 1, wherein the plant is selected from *Perilla fructescens* Britton; *P. frutescens* Britton var. crispa Dec. f. purpurea Makino; *P. frutescens* Britton var. crispa Dec. f. viridis Makino; *P. frutescens* Britton var. crispa Dec. f. discolor Makino; *P. frutescens* var. crispa Dec. f. crispa Makino; *P. frutescens* Britton var. crispa Dec. f. viridis-crispa Makino; *P. frutescens* Britton var. hirtella Makino et Nemoto; *P. citriodora* Nakai and variants thereof.

4. The process of claim 1, wherein the extracting water has an alkaline pH.

5. The process of claim 4, wherein the pH is 7–10.

6. The process of claim 1, wherein the supernatant is fractionated by ultrafiltration.

7. The process of claim 6, wherein the ultrafiltration is effected by using a membrane for retaining substances having a molecular weight of more than 100,000.

8. The process of claim 1, wherein the fractionation is effected by adding to the supernatant one member selected from organic solvents miscible with water and incapable of dissolving the said interferon inducer and ammonium salts so as to form a precipitate containing a major portion of the said interferon inducer.

9. The process of claim 8, wherein the organic solvent is selected from methanol, ethanol, propanol, butanol, acetone and mixture thereof at a concentration of 40–80 w/v %.

10. The process of claim 8, wherein the ammonium salt is selected from ammonium chloride, ammonium sulfate and cetylmetylammonium bromide at a concentration of 20–50 w/v %.

11. An amorphous whitish powder effective as an interferon inducer produced by the process of claim 1.

12. The interferon inducer of claim 11 having a molecular weight of from about 100,000 to about 3,000,000.

13. The interferon inducer of claim 11 which has a molecular weight of about 200,000 to 1,000,000.

* * * * *